United States Patent
Kunzler et al.

(10) Patent No.: US 6,759,496 B2
(45) Date of Patent: Jul. 6, 2004

(54) POLY(2-OXAZOLINE) BIOMEDICAL DEVICES

(75) Inventors: Jay F. Kunzler, Canandaigua, NY (US); Yu-Chin Lai, Pittsford, NY (US); Joseph A. McGee, Rochester, NY (US); Paul L. Valint, Jr., Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 244 days.

(21) Appl. No.: 10/008,441

(22) Filed: Dec. 6, 2001

(65) Prior Publication Data

US 2002/0075448 A1 Jun. 20, 2002

Related U.S. Application Data

(60) Provisional application No. 60/256,658, filed on Dec. 18, 2000.

(51) Int. Cl.$^7$ .............................................. C08F 126/00
(52) U.S. Cl. ....................................................... 526/312
(58) Field of Search ........................................ 526/312

(56) References Cited

U.S. PATENT DOCUMENTS

| | | | |
|---|---|---|---|
| 4,771,089 A | 9/1988 | Ofstead | 524/41 |
| 4,859,719 A | 8/1989 | Ofstead | 523/108 |
| 5,034,461 A | 7/1991 | Lai et al. | 525/100 |
| 5,260,000 A | 11/1993 | Nandu et al. | 264/2.1 |
| 5,352,714 A | 10/1994 | Lai et al. | 523/107 |
| 5,357,013 A | 10/1994 | Bambury et al. | 526/260 |
| 5,374,662 A | 12/1994 | Lai et al. | 522/172 |
| 5,387,662 A | 2/1995 | Kunzler et al. | 526/245 |
| 5,610,252 A | 3/1997 | Bambury et al. | 526/279 |
| 5,760,100 A | 6/1998 | Nicholson et al. | 523/106 |
| 5,760,100 A | 11/2000 | Nicholson et al. | 523/106 |
| 6,447,920 B1 * | 9/2002 | Chabrecek et al. | 428/423.1 |

OTHER PUBLICATIONS

Chujo, et al.; Synthesis of Nonionic Hydrogel, Lipogel, and Amphigel by Copolymerization of 2–Oxazolines and a Bisoxazoline;Macromolecules, vol. 23; No. 5, 1990; p. 1234–1237.

Uyama, et al.; Emulsion Copolymerization of Styrene with Amphiphilic Poly(2–oxazoline) Macromonomer Bearing Ammonio Group at the Chain End; Bull. Chem. Soc. Jpn. vol. 66 No. 10; p. 3124–3127.

Kobayashi, et al.; Synthesis of Acryl– and Methacryl– Type Macromonomers and Telechelics by Utilizing Living Polymerization of 2–Oxazolines; Macromolecules, vol. 22, No. 7, 1989, p. 2878–2884.

* cited by examiner

*Primary Examiner*—Bernard Lipman
(74) *Attorney, Agent, or Firm*—John E. Thomas

(57) ABSTRACT

Biomedical devices are formed from the polymerization product of a monomeric mixture including a poly(2-oxazoline) endcapped with an ethylenically unsaturated radical, such as poly(2-oxazoline) macromonomers and telechelics. Preferred devices are ophthalmic lenses, especially contact lenses and intraocular lenses.

19 Claims, No Drawings

POLY(2-OXAZOLINE) BIOMEDICAL DEVICES

BACKGROUND OF THE INVENTION

The present invention generally relates to biomedical devices, and especially ophthalmic lenses that are intended for direct placement on or in the eye such as contact lenses or intraocular lenses, where the devices and lenses are made of a poly(2-oxazoline) homopolymer or copolymer.

Hydrogels represent a desirable class of materials for many biomedical device applications, including contact lenses and intraocular lenses. Hydrogels are hydrated, cross-linked polymeric systems that contain water in an equilibrium state. Typically, a monomeric mixture including at least one hydrophilic monomer is polymerized by free radical polymerization. One of the hydrophilic monomers may function as a crosslinking agent (a crosslinker being defined as a monomer having multiple polymerizable functionalities) or a separate crosslinking comonomer may be employed. One class of hydrogels are silicone hydrogels, which are characterized by the inclusion of a silicone-containing material in the monomeric mixture.

U.S. Pat. Nos. 5,352,714 (Lai et al.) and 5,357,013 (Bambury et al.) disclose certain 2-oxazolin-5-one monomers having 2-vinyl substitution that are useful as wetting agents in ophthalmic lens polymeric materials, including silicone hydrogel materials. A representative 2-oxazolin-5-one compound disclosed in these patents is 2-vinyl-4,4-dimethyl-2-oxazolin-5-one (VDMO).

The present invention provides a novel biomedical devices based on the subject materials. These materials are biocompatible and may be manufactured (for example, molded or machined) into a desired shape, and exhibit suitable physical properties for prolonged contact with the body. The materials are also optically clear and suitable for ophthalmic lens applications.

SUMMARY OF THE INVENTION

This invention provides a biomedical device formed from the polymerization product of a monomeric mixture comprising a poly(2-oxazoline) endcapped with an ethylenically unsaturated radical. Preferred devices are ophthalmic lenses intended for direct contact with the eye, especially contact lenses and intraocular lenses.

A first preferred class of poly(2-oxazoline) materials is based on macromonomers of the formula:

$$CH_3-(NCH_2CH_2)_n-R$$
$$|$$
$$COR'$$

where R is a polymerizable, ethylenically unsaturated radical;
R' is selected from the group consisting of alkyl, haloalkyl, alkene, alkyne, cycloalkyl, halocycloalkyl, aryl, haloaryl, aralkyl and haloaralkyl; and
n is at least 2.

A second preferred class of poly(2-oxazoline) materials is based on telechelics of the formula:

$$R-(CH_2CH_2N)_x-Z-(NCH_2CH_2)_y-R$$
$$|\quad\quad\quad|$$
$$COR'\quad COR'$$

where each R is independently a polymerizable, ethylenically unsaturated radical;
each R' is independently selected from the group consisting of alkyl, haloalkyl, alkene, alkyne, cycloalkyl, halocycloalkyl, aryl, haloaryl, aralkyl and haloaralkyl;
Z is a divalent linkage; and
each of x and y is at least 1.

DETAILED DESCRIPTION OF PREFERRED EMBODIMENTS

This invention provides a novel class of biomedical materials. Biomedical applications include shaped articles and coatings intended for direct contact with body tissue, including artificial ureters, diaphragms, intrauterine devices, heart valves, catheters, denture liners, prosthetic devices and coatings therefor. The materials are especially useful for ophthalmic lens applications, where the lens is intended for direct placement in or on the eye, including intraocular devices and contact lenses.

The materials are based on polymers of poly(2-oxazoline) endcapped with a polymerizable, ethylenically unsaturated radical. The term "poly(2-oxazoline)" denotes the ring-opening reaction product of 2-oxazoline, such reaction product including multiple amine units from the ring-opening reaction. The term "endcapped with an ethylenically unsaturated radical" and like terms denote that the poly(2-oxazoline) moiety has at least one terminal radical covalently bonded thereto that includes ethylenic unsaturation. This terminal ethylenically unsaturated radical is polymerizable by free radical polymerization.

A first preferred class of poly(2-oxazoline) materials is based on macromonomers of the formula:

$$CH_3-(NCH_2CH_2)_n-R \quad\quad (I)$$
$$|$$
$$COR'$$

where R is the polymerizable, ethylenically unsaturated radical;
R' is selected from the group consisting of alkyl, haloalkyl, alkene, alkyne, cycloalkyl, halocycloalkyl, aryl, haloaryl, aralkyl and haloaralkyl; and
n is at least 2.

Representative R groups may be represented by the formula:

$$\begin{array}{c}R_{23}\\R_{24}\\\diagup\\=\\\diagdown\\R_{24}\end{array}(CH_2)_b-(X)_c-(Q)_d-(Ar)_e-R_{25}-$$

wherein:
$R_{23}$ is hydrogen or methyl;
each $R_{24}$ is hydrogen, an alkyl radical having 1 to 6 carbon atoms, or a —CO—Y— $R_{26}$ radical wherein Y is —O—, —S— or —NH—;
$R_{25}$ is a single bond or a divalent alkylene radical having 1 to 10 carbon atoms;
$R_{26}$ is an alkyl radical having 1 to 12 carbon atoms;
X denotes —CO— or —OCO—;
Q denotes —O— or —NH—;
Ar denotes an aromatic radical having 6 to 30 carbon atoms; b is 0 to 6; c is 0 or 1; d is 0 or 1; and e is 0 or 1. Preferred R radicals include (meth)acrylate, (meth)acrylamide, allyl and styrene radicals. As used herein, the term "(meth)" denotes optional methyl substitution, for example, the term "(meth)acrylate" denotes both methacrylate and acrylate.

Preferred R' radicals include $C_{1-C6}$ alkyl and phenyl.

The macromonomers may be prepared according to the following general reaction scheme A:

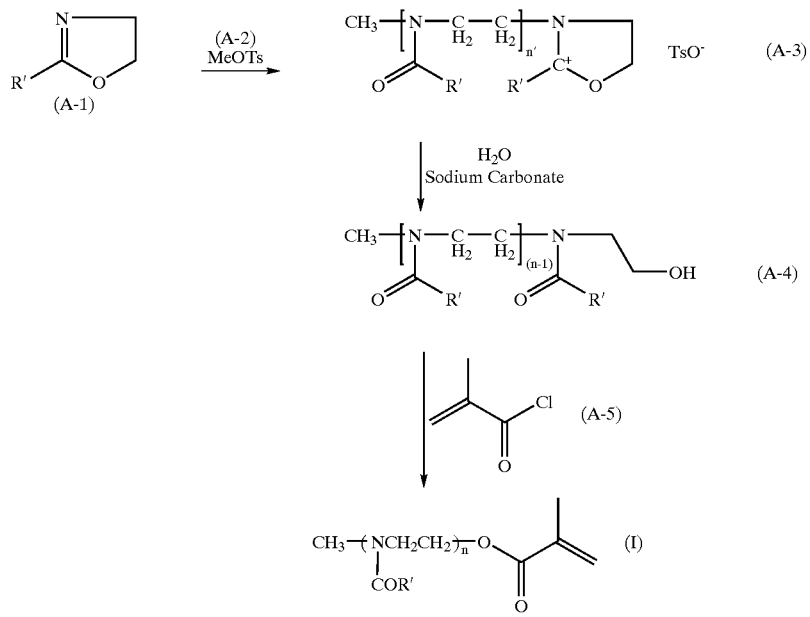

In reaction scheme A, the 2-substituted-2-oxazoline (A-1) is subjected to catalyzed ring opening polymerization using, for example, methyl-p-toluenesulfonate (A-2), followed by reaction of the resultant product (A-3) with a water/sodium carbonate mixture to prepare the hydroxy-terminated poly(2-oxazoline) (A-4). The hydroxy-terminated poly(2-oxazoline) (A-4) is then reacted with an ethylenically unsaturated radical, such as methacryloyl chloride (A-5) to obtain the macromonomer of Formula (I). Other representative ethylenically unsaturated radicals that are reactive with the hydroxyl radical on the hydroxy-terminated poly(2-oxazoline) include: isocyanatoethyl (meth)acrylate to provide a (meth)acrylate end group; or vinyl chloro formate to provide a vinyl end group.

A second preferred class of poly(2-oxazoline) materials is based on telechelics of the formula:

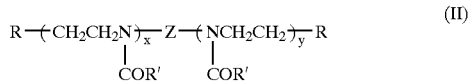

where each R is independently a polymerizable, ethylenically unsaturated radical;
each R' is independently selected from the group consisting of alkyl, haloalkyl, alkene, alkyne, cycloalkyl, halocycloalkyl, aryl, haloaryl, aralkyl and haloaralkyl;
Z is a divalent linkage; and
each of x and y is at least 1.

Representative R and R' radicals are similar to those in Formula (I). Representative Z linkages include a single bond and $C_{1-C_6}$ alkylene optionally including ether linkages.

The telechelics may be prepared according to the following general reaction scheme:

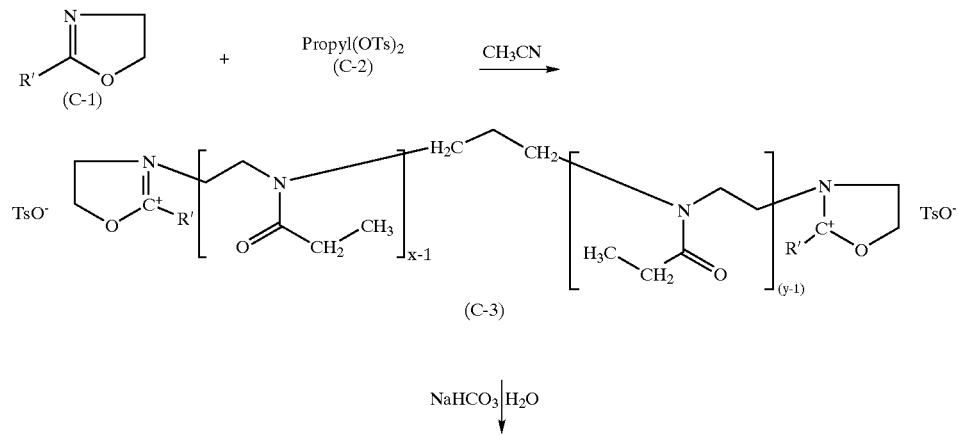

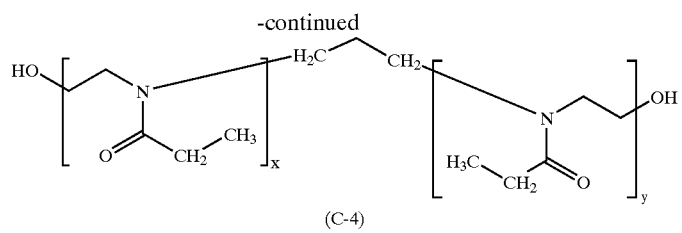

(C-4)

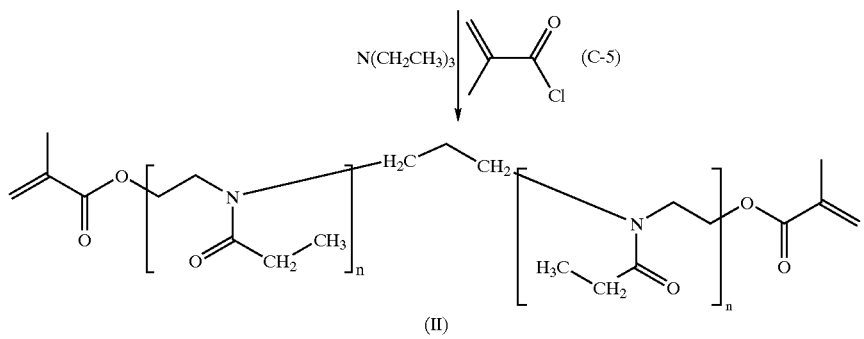

(II)

In reaction scheme C, the 2-substituted-2-oxazoline (C-1) is subjected to catalyzed ring opening polymerization using, for example, propyl-di-p-toluenesulfonate (C-2), followed by reaction of the resultant product (C-3) with a water/sodium carbonate mixture to prepare the dihydroxy-terminated poly(2-oxazoline) (C-4). The dihydroxy-terminated poly(2-oxazoline) (C-4) is then reacted with an ethylenically unsaturated radical, such as methacryloyl chloride (C-5) to obtain the macromonomer of Formula (I). For this reaction scheme, other ethylenically unsaturated radicals that are reactive with the hydroxyl radicals on the dihydroxy-terminated poly(2-oxazoline) (C-4) may be employed. Illustrative 2-substituted-2-oxazoline starting materials for the macromonomers of Formula (I) and the telechelics of Formula (II), for example (A-1) in Scheme A and (C-1) in Scheme C, include: 2-methyl-2-oxazoline, 2-ethyl-2-oxazoline, and 2-phenyl-2-oxazoline.

The poly(2-oxazoline), including the subject macromonomers of Formula (I) and the telechelics of Formula (II), may be polymerized by free radical polymerization to form homopolymers. Alternately, these poly(2-oxazolines) may be copolymerized with a comonomer, the comonomer preferably including ethylenic unsaturatation.

A first class of comonomers that may be included in the initial monomeric mixture containing the subject poly(2-oxazolines) is hydrophilic comonomers. These comonomers include: unsaturated carboxylic acids, such as methacrylic and acrylic acids; (meth)acrylic substituted alcohols, such as 2-hydroxyethyl(meth)acrylate and glyceryl(meth)acrylate; vinyl lactams, such as N-vinyl pyrrolidone; and (meth) acrylamides, such as methacrylamide and N,N-dimethylacrylamide.

A second class of comonomers is silicone-containing comonomers. Such comonomers are useful in preparing a silicone hydrogel having increased oxygen permeability. Representative silicone-containing comonomers include methacryloxypropyltris(trimethylsiloxy)silane (TRIS), pentamethyldisiloxanyl methylmethacrylate, tris (trimethylsiloxy) methacryloxy propylsilane, phenyltetramethyl-disiloxanylethyl acrylate, methyldi(trimethylsiloxy) methacryloxymethyl silane, 3-[tris (trimethylsiloxy)silyl] propyl vinyl carbamate, 3-[tris (trimethylsiloxy)silyl] propyl allyl carbamate, and 3-[tris (trimethylsiloxy)silyl] propyl vinyl carbonate. Additional silicone-containing monomers include prepolymers including a polysiloxane unit, such as a poly(dimethylsiloxane) unit, and endcapped with at least two ethylenically unsaturated radicals. One example is compounds of the formula:

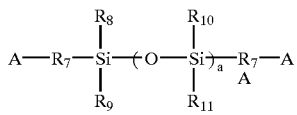

wherein:
each A is independently an ethylenically unsaturated radical;
each $R_7$ is independently an alkylene group having 1 to 10 carbon atoms wherein the carbon atoms may include ether linkages therebetween;
each $R_8$ through $R_{11}$ is independently selected from monovalent hydrocarbon radicals or halogen substituted monovalent hydrocarbon radicals having 1 to 18 carbon atoms which may include ether linkages therebetween; and
a is an integer equal to or greater than 1.

Other examples of polysiloxane-containing prepolymers are disclosed in U.S. Pat. Nos. 5,034,461; 5,260,000; 5,374,662; 5,387,662; 5,610,252; and 5,760,100.

Generally, for forming hydrogel articles, a crosslinking monomer is employed in the monomeric mixture. The described telechelic poly(2-oxazolines) include multiple terminal ethylenic unsaturated radicals, and therefore, these monomeric materials may function as a crosslinking agent. If desired, an additional crosslinking comonomer may be included in the initial monomeric mixture. Examples of crosslinking agents include di- or tri-(meth)acrylates of diols or triols, such as ethyleneglycoldi(meth)acrylate, hexane-1,6-diol-di(meth)acrylate, butane-1,4-diol-di(meth)acrylate and neopentylglycol di(meth)acrylate; bis(meth)acrylamides; diallyl compounds, such as diallyl phthalate; and divinylbenzene.

Although not required, compositions within the scope of the present invention may include comonomers functioning as a toughening agent to increase physical strength of the resultant copolymer. Examples of toughening agents are: cycloalkyl (meth)acrylates, such as isobornyl(meth)acrylate and 4-t-butyl-2-hydroxycyclohexyl (meth)acrylate; and alkyl and haloalkyl (meth)acrylates, such as octafluoropentyl(meth)acrylate and butyl(meth)acrylate.

The subject telechelic or macromonomer can be cast into shaped biomedical articles, such as contact lenses or intraocular lenses, by conventional methods commonly used in polymerizing ethylenically unsaturated monomeric materials. As one example, the liquid or semi-liquid monomeric mixture containing the subject telechelic or macromonomer (and any comonomer) may be charged to a mold of the desired shape, followed by polymerizing (or curing) the mixture in the mold. Various processes are known for curing a monomeric mixture in the production of contact lenses, including spincasting and static casting. Spincasting methods involve charging the monomer mixture to a mold, and spinning the mold in a controlled manner while exposing the monomer mixture to a radiation source such as UV light. Static casting methods involve charging the monomer mixture between two mold sections, one mold section shaped to form the anterior lens surface and the other mold section shaped to form the posterior lens surface, and curing the monomer mixture by exposure to a radiation source and/or heat. Other known methods for forming contact lenses or intraocular lenses involve forming articles in the form of buttons (or blanks) and then lathe cutting the buttons into lenses.

Polymerization may be facilitated by exposing the mixture to heat and/or radiation, such as ultraviolet light, visible light, or high energy radiation. A polymerization initiator may be included in the mixture to facilitate the polymerization step. Representative free radical thermal polymerization initiators are organic peroxides, such as acetal peroxide, lauroyl peroxide, decanoyl peroxide, stearoyl peroxide, benzoyl peroxide, tertiarylbutyl peroxypivalate, peroxydicarbonate, and the like. Representative UV initiators are those known in the field such as, benzoin methyl ether, benzoin ethyl ether, Darocure 1173, 1164, 2273, 1116, 2959, 3331 (EM Industries) and Igracure 651 and 184 (Ciba-Geigy), and the like. Generally, the initiator will be employed in the monomeric mixture at a concentration of about 0.01 to 1 percent by weight of the total mixture.

Optionally, the monomeric mixture may include, in addition to the telechelic or macromonomer and any comonomer, a diluent that is ultimately replaced with water when the polymerization product is hydrated to form a hydrogel. In addition, the monomeric mixture may include various other optional components, such as colorants or UV-absorbing agents.

Although various preferred embodiments have been illustrated, many other modifications and variations of the present invention are possible to the skilled practitioner. It is therefore understood that, within the scope of the claims, the present invention can be practiced other than as herein specifically described.

We claim:

1. A biomedical device cast and formed from the polymerization product of a monomeric mixture comprising a poly(2-oxazoline) endcapped with an ethylenically unsaturated radical.

2. The device of claim 1, which is an ophthalmic lens.

3. The lens of claim 2, wherein the poly(2-oxazoline) is a macromonomer of the formula:

$$CH_3-(NCH_2CH_2)_n-R$$
$$|$$
$$COR'$$

where R is a polymerizable, ethylenically unsaturated radical;

R' is selected from the group consisting of alkyl, haloalkyl, alkene, alkyne, cycloalkyl, halocycloalkyl, aryl, haloaryl, aralkyl and haloaralkyl; and n is at least 2.

4. The lens of claim 3, wherein R is $$\begin{array}{c} R_{23} \\ R_{24} \\ \diagup \\ \diagdown \\ R_{24} \end{array} (CH_2)_b-(X)_c-(Q)_d-(Ar)_e-R_{25}-$$

wherein:

$R_{23}$ is hydrogen or methyl;

each $R_{24}$ is hydrogen, an alkyl radical having 1 to 6 carbon atoms, or a —CO—Y—$R_{26}$ radical wherein Y is —O—, —S— or —NH—;

$R_{25}$ is a single bond or a divalent alkylene radical having 1 to 10 carbon atoms;

$R_{26}$ is an alkyl radical having 1 to 12 carbon atoms;

X denotes —CO— or —OCO—;

Q denotes —O— or —NH—;

Ar denotes an aromatic radical having 6 to 30 carbon atoms;

b is 0 to 6; c is 0 or 1; d is 0 or 1; and e is 0 or 1.

5. The lens of claim 4, wherein R is selected from the group consisting of (meth)acrylate, (meth)acrylamide, allyl and styrene radicals.

6. The lens of claim 3, wherein R' is selected from the group consisting of $C_1$–$C_6$ alkyl and phenyl.

7. The lens of claim 2, wherein the poly(2-oxazoline) is a telechelic of the formula:

$$R-(CH_2CH_2N)_x-Z-(NCH_2CH_2)_y-R$$
$$| \qquad \qquad |$$
$$COR' \qquad COR'$$

where each R is independently a polymerizable, ethylenically unsaturated radical;

each R' is independently selected from the group consisting of alkyl, haloalkyl, alkene, alkyne, cycloalkyl, halocycloalkyl, aryl, haloaryl, aralkyl and haloaralkyl;

Z is a divalent linkage; and each of x and y is at least 1.

8. The lens of claim 7, wherein R is $$\begin{array}{c} R_{23} \\ R_{24} \\ \diagup \\ \diagdown \\ R_{24} \end{array} (CH_2)_b-(X)_c-(Q)_d-(Ar)_e-R_{25}-$$

wherein:

$R_{23}$ is hydrogen or methyl;

each $R_{24}$ is hydrogen, an alkyl radical having 1 to 6 carbon atoms, or a —CO—Y—$R_{26}$ radical wherein Y is —O—, —S— or —NH—;

$R_{25}$ is a single bond or a divalent alkylene radical having 1 to 10 carbon atoms;

$R_{26}$ is an alkyl radical having 1 to 12 carbon atoms;

X denotes —CO— or —OCO—;

Q denotes —O— or —NH—;

Ar denotes an aromatic radical having 6 to 30 carbon atoms;

b is 0 to 6; c is 0 or 1; d is 0 or 1; and e is 0 or 1.

9. The lens of claim 8, wherein R is selected from the group consisting of (meth)acrylate, (meth)acrylamide, allyl and styrene radicals.

10. The lens of claim 7, wherein R' is selected from the group consisting of $C_1$–$C_6$ alkyl and phenyl.

11. The lens of claim 7, wherein Z is selected from the group consisting of a single bond and $C_1$–$C_6$ alkylene optionally including ether linkages.

12. The lens of claim 2, wherein the monomeric mixture further comprises at least one hydrophilic monomer selected from the group consisting of ethylenically unsaturated carboxylic acids, (meth)acrylic substituted alcohols, vinyl lactams, and (meth)acrylamides.

13. The lens of claim 12, wherein the monomeric mixture comprises at least one hydrophilic monomer selected from the group consisting of (meth)acrylic acid, 2-hydroxyethyl (meth)acrylate, glyceryl(meth)acrylate, N-vinyl pyrrolidone, methacrylamide and N,N-dimethylacrylamide.

14. The lens of claim 2, wherein the monomeric mixture further comprises at least one silicone-containing monomer.

15. The lens of claim 14, wherein the monomeric mixture comprises at least one silicone-containing monomer selected from the group consisting of methacryloxypropyl tris(trimethylsiloxy)silane, pentamethyldisiloxanyl methylmethacrylate, tris(trimethylsiloxy) methacryloxy propylsilane, phenyltetramethyl-disiloxanylethyl acrylate, methyldi(trimethylsiloxy)methacryloxymethyl silane, 3-[tris(trimethylsiloxy)silyl] propyl vinyl carbamate, 3-[tris(trimethylsiloxy)silyl] propyl allyl carbamate, and 3-[tris(trimethylsiloxy)silyl] propyl vinyl carbonate.

16. The lens of claim 2, which is a contact lens.

17. The lens of claim 2, which a hydrogel contact lens.

18. The lens of claim 2, which is an intraocular lens.

19. The lens of claim 18, which is a hydrogel intraocular lens.

* * * * *